(12) United States Patent
Dollinger et al.

(10) Patent No.: US 6,664,253 B2
(45) Date of Patent: *Dec. 16, 2003

(54) NEUROKININ ANTAGONISTS

(75) Inventors: Horst Dollinger, Ingelheim (DE);
Franz Esser, Ingelheim (DE); Birgit Jung, Schwabenheim (DE); Gerd Schnorrenberg, Biberbach (DE); Kurt Schromm, Ingelheim (DE); Georg Speck, Ingelhem (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/978,639

(22) Filed: Oct. 16, 2001

(65) Prior Publication Data

US 2002/0115666 A1 Aug. 22, 2002

Related U.S. Application Data

(60) Provisional application No. 60/250,660, filed on Dec. 1, 2000.

(30) Foreign Application Priority Data

Oct. 17, 2000 (DE) .......................................... 100 51 321

(51) Int. Cl.$^7$ ..................... C07D 211/58; C07D 401/12; C07D 413/12; A61K 31/495; A61P 37/08
(52) U.S. Cl. ..................... 514/228.8; 514/274; 514/315; 514/317; 514/321; 514/326; 544/96; 544/97; 544/311; 546/192; 546/195; 546/196; 546/197; 546/207; 546/208; 546/210; 546/213
(58) Field of Search ................................. 546/195, 196, 546/197, 207, 208, 210, 213, 192; 544/96, 97, 311; 514/228.8, 274, 317, 321, 326, 315

(56) References Cited

FOREIGN PATENT DOCUMENTS

| WO | WO 96 32386 | 10/1996 |
|---|---|---|
| WO | WO 97 32865 | 9/1997 |

*Primary Examiner*—Bruce Kifle
(74) *Attorney, Agent, or Firm*—Robert P. Raymond; Philip I. Datlow; Alan R. Stempel

(57) ABSTRACT

The invention relates to new compounds of formula I

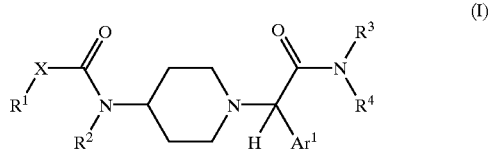

or the pharmaceutically acceptable salts thereof,
wherein
$R^1$, $R^2$, $R^3$, $R^4$, X and $Ar^1$ have the meanings given in the specification, as well as the preparation and use thereof. The new compounds are valuable neurokinin (tachykinin) antagonists.

26 Claims, No Drawings

NEUROKININ ANTAGONISTS

RELATED APPLICATIONS

Benefit of U.S. Provisional Application Serial No. 60/250,660, filed on Dec. 1, 2000 is hereby claimed, and said Provisional Application is herein incorporated by reference.

FIELD OF THE INVENTION

The invention relates to new compounds of formula I,

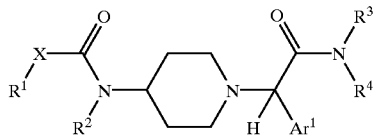

(I)

wherein the groups Ar, $R^1$, $R^2$, $R^3$, $R^4$ and X have the meanings given in the claims and specification, processes for preparing them as well as their use as pharmaceutical compositions, and the pharmaceutically acceptable salts thereof, processes for preparing them and pharmaceutical compositions containing these compounds. The compounds are valuable neurokinin (tachykinin) antagonists.

BACKGROUND OF THE INVENTION

The compounds of formula I are partly covered by the broad general formula of International Patent Application WO96/32386. However, this does not disclose any compounds in which the amide group is substituted with a 2-phenyl-ethyl group and the piperidyl group in the 4 position is substituted with a substituted urethane or urea group. The compounds described in this international patent application are neurokinin antagonists with a broad spectrum of activity.

The problem of the present invention is to provide new neurokinin antagonists with an enhanced activity. This problem is now solved according to the invention by the preparation of the new compounds of formula I.

DETAILED DESCRIPTION OF THE INVENTION

Surprisingly it has been found that the activity of the new $NK_1$ receptor antagonists of formula I is dramatically increased compared with the known compounds.

The invention therefore relates to new compounds of formula I

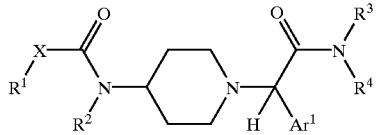

(I)

or the pharmaceutically acceptable salts thereof,
wherein
$R^1$ denotes $C_1$–$C_6$-alkyl or $Ar^2$,
$R^2$ denotes hydrogen, $C_1$–$C_6$-alkyl or $C_3$–$C_6$-cycloalkylmethyl, or
$R^1$ and $R^2$ taken together denote a $C_2$–$C_3$-alkylenediyl group optionally substituted by one or two oxo groups (=O),
X denotes O or $NR^5$,
$Ar^1$ and $Ar^2$ independently of one another denote unsubstituted phenyl or phenyl which is 1- to 5-substituted by halogen, hydroxy, $C_1$–$C_4$-alkyl, $C_1$–$C_4$-alkoxy, $C_1$–$C_4$-fluoroalkyl, $C_1$–$C_4$-fluoroalkoxy or —OCH$_2$O—;
$R^3$ denotes 2-phenyl-ethyl, wherein the phenyl group may be substituted by 1 to 3 substituents, while the substituents, independently of one another, are selected from among halogen, hydroxy, $C_1$–$C_4$-alkyl, $C_1$–$C_4$-alkoxy, $C_1$–$C_4$-fluoroalkyl, $C_1$–$C_4$-fluoroalkoxy;
$R^4$ denotes hydrogen, $C_1$–$C_4$-alkyl, $C_3$–$C_8$-cycloalkyl, $CH_2COOH$, —$CH_2C(O)NH_2$, —OH or phenyl-$C_1$–$C_4$-alkyl; and
$R^5$ denotes hydrogen or $C_1$–$C_6$-alkyl.

In the foregoing and in what is to follow, the terms "alkyl" and "alkoxy" as used with reference to the groups $R^1$, $R^2$, $R^3$, $R^4$ or the substituents of $Ar^1$ or $Ar^2$ denote straight-chain or branched, saturated hydrocarbon groups with up to 6 carbon atoms, preferably 1 to 4 carbon atoms, particularly methyl, ethyl, n-propyl, 1-propyl, n-butyl, tert-butyl, methoxy, ethoxy, n-propoxy or i-propoxy.

In the foregoing and in what is to follow, the terms "fluoroalkyl" and "fluoroalkoxy" as used with reference to the group $R^3$ or the substituents of Ar denote straight-chain or branched, fluorine-substituted hydrocarbon groups with up to 4 carbon atoms and up to 9 fluorine atoms, preferably 1 or 2 carbon atoms and up to 5 fluorine atoms, particularly trifluoroethyl, pentafluoroethyl, 2,2,2-trifluoroethyl, 2-fluoroethyl, difluoromethoxy, trifluoromethoxy, pentafluoroethoxy, 2,2,2-trifluoroethoxy or 2-fluoroethoxy.

The compounds according to the invention are valuable neurokinin (tachykinin) antagonists which have substance P-antagonistic properties. They are useful for treating and preventing neurokinin-mediated illnesses and additionally have a dramatically increased effect.

Compounds of general formula I may have acid groups, mainly carboxyl groups, and/or basic groups such as, for example, amino functions. Compounds of general formula I may therefore be in the form of internal salts, salts with pharmaceutically useable inorganic acids such as hydrochloric acid, sulphuric acid, phosphoric acid, sulphonic acid or organic acids (such as for example maleic acid, fumaric acid, citric acid, tartaric acid or acetic acid) or salts with pharmaceutically useable bases such as alkali or alkaline earth metal hydroxides or carbonates, zinc or ammonium hydroxides or organic amines such as, for example, diethylamine, triethylamine, triethanolamine etc.

The compounds according to the invention may occur as racemates, or they may be obtained as pure enantiomers, i.e. in the (R)- or (S)-form. Compounds which occur as racemates or as the (S)-form are preferred.

The compounds according to the invention are valuable neurokinin (tachykinin) antagonists which have substance P-antagonistic properties. They are useful for treating and preventing neurokinin-mediated illnesses:

Treatment or prevention of inflammatory and allergic complaints of the airways, such as asthma, chronic bronchitis, hyperreactive airways, emphysema, rhinitis, COPD, pulmonary hypertension, cystic fibrosis, coughs;
of the eyes, such as conjunctivitis and iritis,
of the skin, such as dermatitis in contact eczema, neurodermatitis, pruritus, urticaria, psoriasis, sunburn, burns, insect bites, rosacea, itching, sensitive or hypersensitive skin, of the gastrointestinal tract, such as gastric and duodenal ulcers, ulcerative colitis, Crohn's disease, inflammatory bowel disease, irritable colon, Hirschsprung's disease, motility problems;
of the joints or bones, such as rheumatoid arthritis, reactive arthritis, arthrosis, osteoporosis and Reiter's syndrome; of the bladder, such as irritable bladder, incontinence, urinary urgency, urethritis, colic and cystitis.

Also for the treatment of diseases of the central nervous system such as dementia, Alzheimer's disease, schizophrenia, psychoses, anxiety states, alcohol or drug dependency, sexual dysfunctions, eating disorders, depression, headaches (e.g. migraine or tension headaches), epilepsy; Parkinson's disease, stroke,
treatment of Herpes zoster as well as postherpetic pain, tumours, collagenoses, a dysfunction of the deferent urinary tracts, haemorrhoid, nausea and vomiting, triggered for example by radiation or cytostatic therapy or motion, and painful conditions of all kinds.

The invention therefore also relates to the use of the compounds of formula I as curative agents and pharmaceutical preparations which contain these compounds. They are preferably used on humans. The compounds according to the invention may be given intravenously, subcutaneously, intramuscularly, intraperitoneally, intranasally, by inhalation, transdermally, optionally assisted by iontophoresis or enhancers known from the literature, and by oral route.

For parenteral administration the compounds of formula I or their physiologically acceptable salts, may be put into solution, suspension or emulsion, possibly with substances conventionally used for this purpose such as solubilisers, emulsifiers or other adjuvants. Suitable solvents include, for example: water, physiological saline solutions or alcohols, e.g. ethanol, propanediol or glycerol, sugar solutions such as glucose or mannitol solutions or a mixture of various solvents.

In addition, the compounds may be administered by the use of implants, e.g. of polylactide, polyglycolide or polyhydroxybutyric acid or intranasal preparations.

Compounds of formula I, wherein $R^4$ denotes $C_1$–$C_4$-alkyl, particularly methyl, are preferred.

Also preferred are compounds of formula I wherein Ar is unsubstituted phenyl or 2,3-methylenedioxyphenyl, particularly unsubstituted phenyl.

Preferred compounds of formula I are those wherein $R^3$ denotes 2-phenylethyl, wherein the phenyl group may be substituted by 1 to 3 substituents, wherein the substituents are selected independently of one another from among halogen, hydroxy, methyl, methoxy, trifluoromethyl, trifluoromethoxy, particularly wherein $R^3$ is 2-(3,5-bis-trifluoromethylphenyl)-ethyl.

Particularly preferred compounds of formula I are those wherein the group —$NR^3R^4$ is

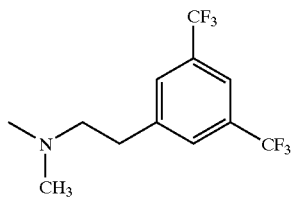

In a preferred aspect the invention relates to compounds of formula I, wherein
$R^1$ denotes a $C_1$–$C_3$-alkyl, particularly methyl, phenyl or $C_1$–$C_3$-alkoxyphenyl group, particularly 4-methoxyphenyl,
X denotes NH, and
$R^2$ denotes a hydrogen atom.

In another preferred aspect the invention relates to compounds of formula I, wherein $R^1$ and $R^2$ taken together denote an ethylene-1,2-diyl, 1-oxoethylene-1,2-diyl, propylene-1,3-diyl, 1-oxopropylene-1,3-diyl or 1-oxobutylene-1,3-diyl group, and
X denotes O, NH or $NCH_3$.

Particularly preferred are NK1 receptor antagonists of formula I, wherein the group

is a group selected from the formulae A-1 to A-8:

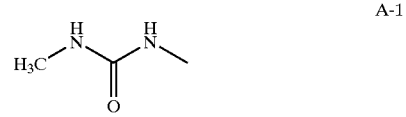
A-1

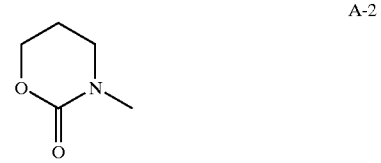
A-2

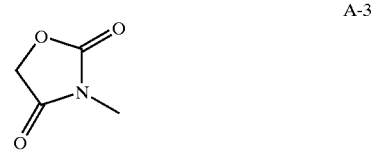
A-3

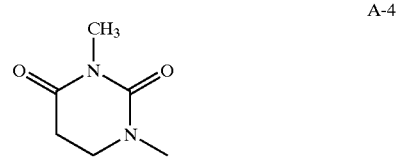
A-4

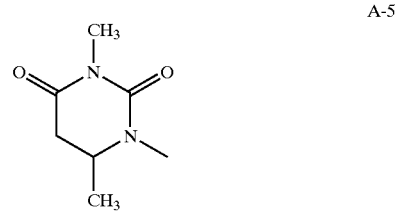
A-5

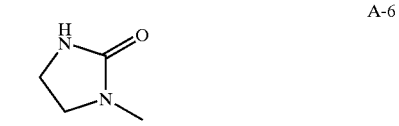
A-6

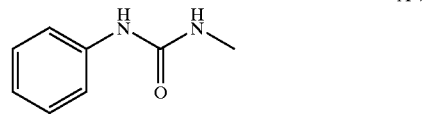
A-7

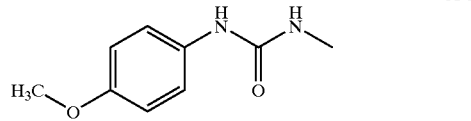
A-8

The following compounds are particularly preferred:

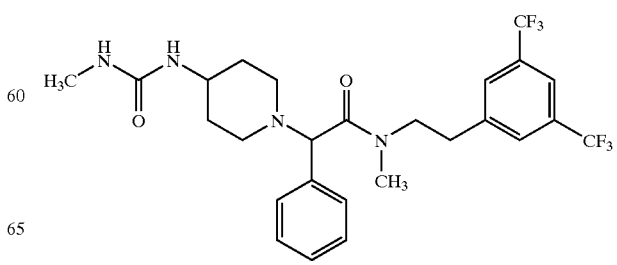

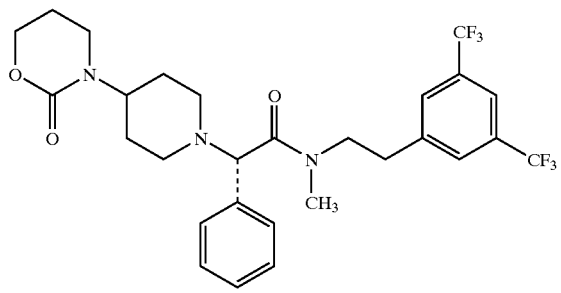

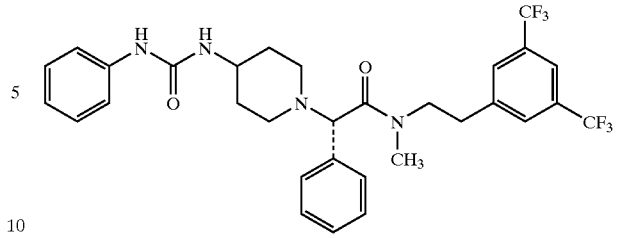

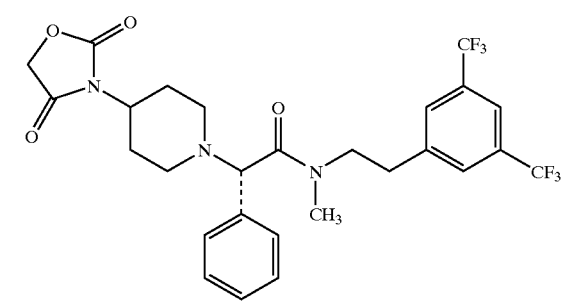

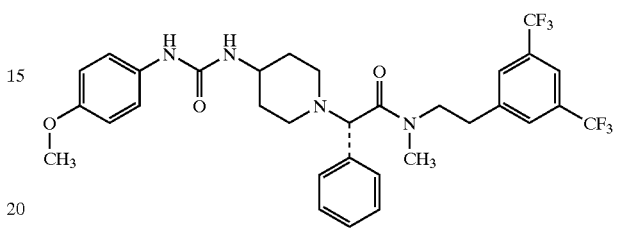

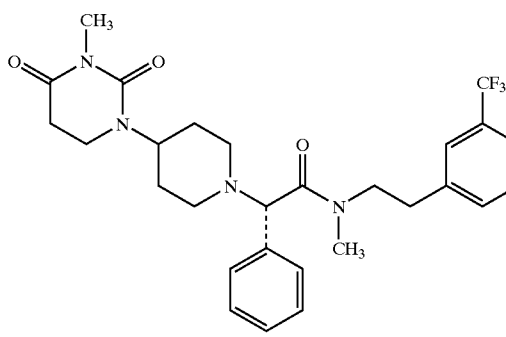

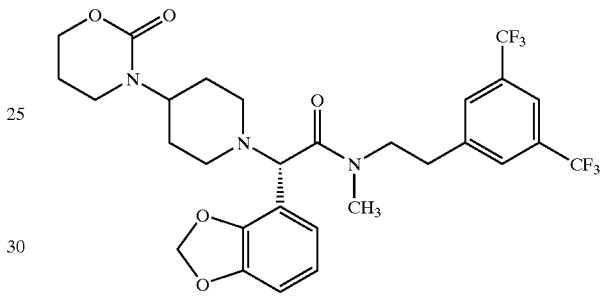

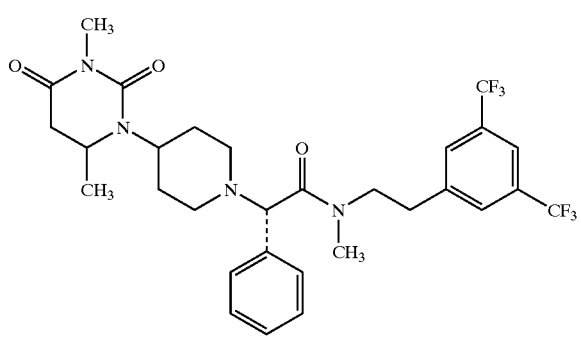

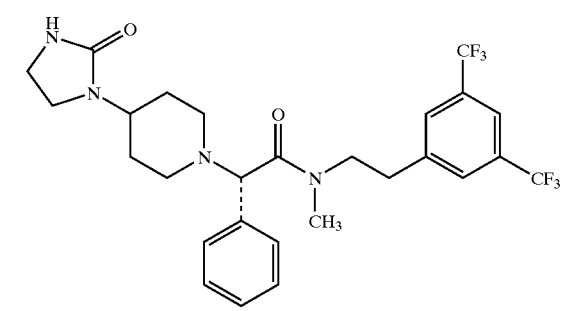

The compounds may be prepared in a manner known per se. Advantageous methods are illustrated and described in the following diagram. The compounds of general formula I may be prepared by reacting an amide of formula II

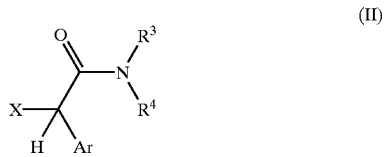

wherein X denotes a suitable leaving group, preferably halogen, alkylsulphonyloxy, particularly methylsulphonyloxy, or arylsulphonyloxy, particularly p-tolylsulphonyloxy, However, the process can be used analogously for all compounds of formula I. The compounds of formula III are known or may be prepared analogously to methods known per se.

Diagram 1

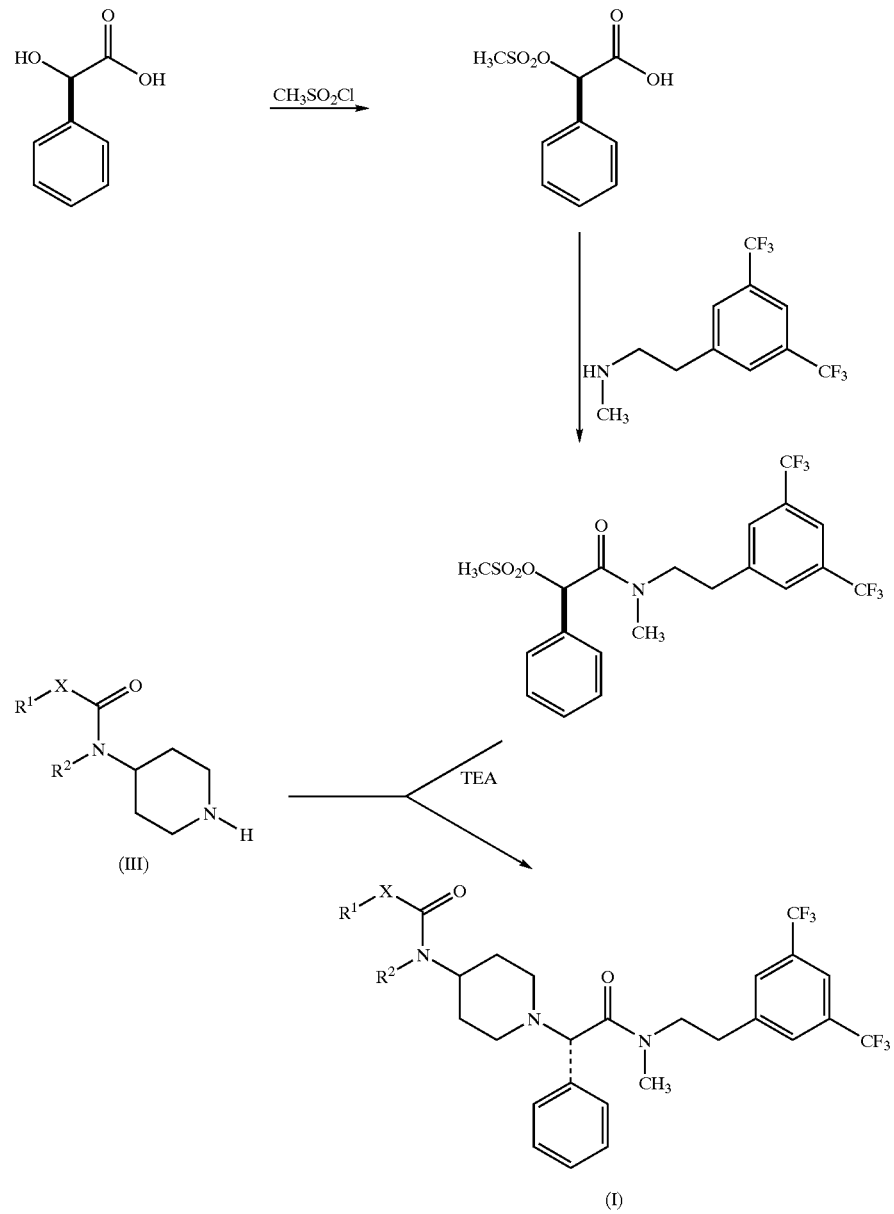

with a piperidine of general formula III

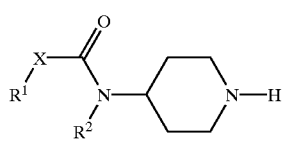

(III)

in an inert solvent in the presence of a base.

This process is illustrated by means of the following Diagram 1 for compounds wherein Ar is phenyl, $R^3$ is bis-(trifluoromethyl)-phenylethyl and $R^4$ is methyl.

The reactant for this piperazine derivative is obtained as shown in Diagram 1, on the right. (R)-Mandelic acid is reacted with methanesulphonic acid halide to obtain (R)-2-(methanesulphonyloxy)-acetic acid. This is then reacted with a coupling reagent and the correspondingly substituted phenethylamine to obtain the corresponding amide, or it is converted into the corresponding acid halide (e.g. with $SOCl_2/SO_2Cl_2$) and then converted with the suitably substituted phenethylamine into the corresponding amide. In the last step the amide thus obtained is reacted with the piperidine derivative described above, while during the substitution of methanesulphonate C-N-linking takes place with simultaneous reversal of the chiral centre. The reaction is carried out in an inert solvent, preferably a polar aprotic solvent such as, for example, DMF, dimethyl acetamide, ethylmethylketone or acetonitrile in the presence of a base, preferably an inorganic base such as, for example, $K_2CO_3$, $NaHCO_3$ or $CaCO_3$, or organic bases such as, for example, tertiary amines, preferably triethylamine, Hünig base, pyridine or N-methylmorpholine, at between 0° C. and 120° C., typically between 10° C. and 80° C. The reaction time is generally between 0.5 h and 48 h.

The compounds and compositions according to the invention will now be illustrated by the Examples which follow. The skilled person is aware that the Examples serve only as an illustration and are not to be regarded as limiting.

A EXAMPLE OF THE SYNTHESIS OF COMPOUNDS ACCORDING TO THE INVENTION

Example 1

N-[2-(3,5-bis-trifluoromethyl-phenyl)-ethyl]-N-methyl-2-[4-(3-methyl-ureido)-piperidin-1-yl]-2-phenyl-acetamide 6.8 g of 4-(3-methylureido)-piperidine are refluxed together with 19.2 g of N-[2-(3,5-bis-trifluoromethyl-phenyl)-ethyl]-2-methanesulphonyloxy-N-methyl-2-phenyl-acetamide (prepared analogously to the method described in WO 99/62893) and 6.8 ml of triethylamine in 400 ml of acetone for 8 hours. Then the solution is evaporated down, combined with saturated sodium hydrogen carbonate solution and extracted with ethyl acetate. The extract is dried, the solvent is eliminated in vacuo and the residue is chromatographed with methylene chloride/methanol 9:1 over silica gel. The fractions found to be uniform by TLC are combined and the solvent is eliminated in vacuo. N-[2-(3,5-bis-tifluormethyl-phenyl)-ethyl]-N-methyl-2-[4-(3-methyl-ureido)-piperidin-1-yl]-2-phenyl-acetamide is crystallised from the residue with ethanolic hydrochloric acid and ether in the form of the hydrochloride, yielding 7.1 g of colourless crystals. $^1$H-NMR (250 MHz, $CD_3OD$) δppm=7.93–7.33 (8H, m); 5.58; 5.38 (1H, 2s); 4.03–2.59 (5H, m); 3.05 (4H, m); 2.98; 2.90 (3H, 2s); 2.74; 2.70 (3H, 2s); NH in the solvent blind peak 4.89; 2.27–1.52 (4H, m). Most signals are split by amide rotation.

Example 2

(S)-N-[2-(3,5-bis-trifluoromethyl-phenyl)-ethyl]-N-methyl-2-[4-(2-oxo-[1.3]oxazinan-3-yl)-piperidin-1-yl]-2-phenyl-acetamide 5.4 g of 4-(2-oxo-[1.3]oxazinan-3-yl)-piperidine are refluxed together with 12.5 g of (R)-N-[2-(3,5-bis-trifluoromethyl-phenyl)-ethyl]-2-methanesulphonyloxy-N-methyl-2-phenyl-acetamide (prepared from D-(–)-mandelic acid) and 4.5 ml of triethylamine in 250 ml of acetone for 6 hours. Then the solution is concentrated by evaporation, combined with saturated sodium hydrogen carbonate solution and extracted with ethyl acetate. The extract is dried, the solvent is eliminated in vacuo and the residue is chromatographed with methylene chloride/methanol 9:1 over silica gel. The fractions found to be uniform by TLC are combined and the solvent is eliminated in vacuo. (S)-N-[2-(3,5-bis-trifluoromethyl-phenyl)-ethyl]-N-methyl-2-[4-(2-oxo-[1,3]oxazinan-3-yl)-piperidin-1-yl]-2-phenyl-acetamide is crystallised from the residue with ethanolic hydrochloric acid and ether in the form of the hydrochloride. 7.5 g of light beige crystals are obtained. $^1$H-NMR (250 MHz, $CD_3OD$) δppm=7.88–7.55 (8H, m); 5.47; 5.28 (1H, 2s); 4.24 (2H, t, J=5.8 Hz); 4.13 (1H, m); 4.06–2.69 (6H, m); 3.04 (4H, m); 3.00; 2.89 (3H, 2s); 2.34–1.71 (6H, m). Most signals are split by amide rotation.

Rotational value $[\alpha]_D^{20}=+36.7°$ (c=1, methanol)

Examples 3 to 10 may be Prepared Analogously

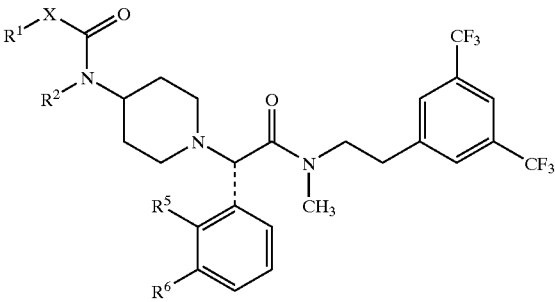

| Example | R$^1$—X— | R$^2$— | R$^5$ | R$^6$ |
|---|---|---|---|---|
| 3 | —O—CH$_2$—C═O— | | H | H |
| 4 | —N(CH$_3$)—C═O—CH$_2$CH$_2$— | | H | H |
| 5 | —N(CH$_3$)—C═O—CH$_2$CH(CH$_3$)— | | H | H |
| 6 | —NH—CH$_2$CH$_2$— | | H | H |
| 7 | phenyl-NH— | H— | H | H |
| 8 | 4-methoxy-phenyl-NH— | H— | H | H |
| 9 | —O—CH$_2$—CH$_2$CH$_2$— | | —O—CH$_2$—O— | |
| 10 | methyl-NH— | H | —O—CH$_2$—O— | |

B Results of Investigations into the Compound According to the Invention:

The receptor affinity to the $NK_1$-receptor (substance P-receptor) is determined on human lymphoblastoma cells (IM-9) with cloned $NK_1$-receptors, by measuring the displacement of $^{125}$I-labelled substance P. The $K_i$-values thus obtained show the efficacy of the compounds.

The compounds according to the invention were compared with the compounds of the following known from International Patent Application WO96/32386:

B-6

B-7

These compounds correspond to the compounds of Examples 6 and 7, wherein the 2-bis-trifluoromethylphenyl-ethyl group has been replaced by a bis-trifluoromethylbenzyl.

The results are listed in Table I:

| Example No. | $K_i$ [nM] |
|---|---|
| 1 | 0.7 |
| 2 | 1.7 |
| 3 | 0.7 |
| 4 | 0.6 |
| 5 | 0.6 |
| 6 | 3.5 |
| B-6 | 165.0 |
| 7 | 0.8 |
| B-7 | 432.0 |

C Formulations of Compounds According to the Invention

Injectable Solution

| 200 mg | active substance* | | |
| --- | --- | --- | --- |
| 1.2 mg | monopotassium dihydrogen phosphate = $KH_2PO_4$ | ) | |
| 0.2 mg | disodium hydrogen phosphate = $NaH_2PO_4 \cdot 2H_2O$ | ) | (buffer) |
| 94 mg | sodium chloride | ) | (isotonic agent) |
| or | | ) | |
| 520 mg | glucose | ) | |
| 4 mg | albumin | | (protease protection) |
| q.s. | sodium hydroxide solution | ) | |
| q.s. | hydrochloric acid | ) | ad pH 6 |
| ad 10 ml | water for injections | | |

Injectable Solution

| 200 mg | active substance* | | |
| --- | --- | --- | --- |
| 94 mg | sodium chloride | | |
| or | | | |
| 520 mg | glucose | | |
| 4 mg | albumin | | |
| q.s. | sodium hydroxide solution | ) | |
| q.s. | hydrochloric acid | ) | ad pH 9 |
| ad 10 ml | water for injections | | |

Lyophilisate

| 200 mg | active substance* |
| --- | --- |
| 520 mg | mannitol (isotonic agent/bulking agent) |
| 4 mg | albumin |
| solvent 1 for lyophilisate | |
| 10 ml | water for injections |
| solvent 1 for lyophilisate | |
| 20 mg | Polysorbat ® 80 = Tween ® 80 (surfactant) |
| 10 ml | water for injections |

*active substance: compound according to the invention, e.g. one of Examples 1 to 8 dose for humans weighing 67 kg: 1 to 500 mg

| 20 mg | Polysorbat ® 80 = Tween ® 80 (surfactant) |
| --- | --- |
| 10 ml | water for injections |

We claim:

1. A compound of formula (I):

$$\text{(I)}$$

or a pharmaceutically acceptable salt thereof, wherein $R^1$ denotes $C_1$–$C_6$-alkyl or $Ar^2$, $R^2$ denotes hydrogen, $C_1$–$C_6$-alkyl or $C_3$–$C_6$-cycloalkylmethyl, or $R^1$ and $R^2$ taken together denote a $C_2$–$C_3$-alkylenediyl group optionally substituted by one or two oxo groups, X denotes O or $NR^5$, $Ar^1$ and $Ar^2$ independently of one another denote unsubstituted phenyl or phenyl which is 1- to 5-substituted by halogen, hydroxy, $C_1$–$C_4$-alkyl, $C_1$–$C_4$-alkoxy, $C_1$–$C_4$-fluoroalkyl, $C_1$–$C_4$-fluoroalkoxy or —$OCH_2O$—;

$R^3$ denotes 2-phenyl-ethyl, wherein the phenyl group may be substituted by 1 to 3 substituents, wherein the substituents, independently of one another, are selected from halogen, hydroxy, $C_1$–$C_4$-alkyl, $C_1$–$C_4$-alkoxy, $C_1$–$C_4$-fluoroalkyl, and $C_1$–$C_4$-fluoroalkoxy; denotes hydrogen, $C_1$–$C_4$-alkyl, $C_3$–$C_8$-cycloalkyl, $CH_2COOH$, —$CH_2C(O)NH_2$, —OH or phenyl-$C_1$–$C_4$-alkyl; and $R^5$ denotes hydrogen or $C_1$–$C_6$-alkyl.

2. A compound according to claim 1, wherein $R^4$ is $C_1$–$C_4$-alkyl.

3. A compound according to claim 1, wherein $Ar^1$ is unsubstituted phenyl or 2,3-methylenedioxyphenyl.

4. A compound according to claim 2, wherein $Ar^1$ is unsubstituted phenyl or 2,3-methylenedioxyphenyl.

5. A compound according to claim 1, wherein $R^3$ denotes 2-phenylethyl, in which the phenyl group is substituted by 1 to 3 substituents, wherein the substituents independently of one another are selected from halogen, hydroxy, methyl, methoxy, trifluoromethyl and trifluoromethoxy.

6. A compound according to claim 2, wherein $R^3$ denotes 2-phenylethyl, in which the phenyl group is substituted by 1 to 3 substituents, wherein the substituents independently of one another are selected from halogen, hydroxy, methyl, methoxy, trifluoromethyl and trifluoromethoxy.

7. A compound according to claim 3, wherein $R^3$ denotes 2-phenylethyl, in which the phenyl group is substituted by 1 to 3 substituents, wherein the substituents independently of one another are selected from halogen, hydroxy, methyl, methoxy, trifluoromethyl and trifluoromethoxy.

8. A compound according to claim 4, wherein $R^3$ denotes 2-phenylethyl, in which the phenyl group is substituted by 1 to 3 substituents, wherein the substituents independently of one another are selected from halogen, hydroxy, methyl, methoxy, trifluoromethyl and trifluoromethoxy.

9. A compound according to claim 1, wherein $R^3$ is 2-(3,5-bis-trifluoromethylphenyl)-ethyl.

10. A compound according to claim 2, wherein $R^3$ is 2-(3,5-bis-trifluoromethylphenyl)-ethyl.

11. (original) A compound according to claim 3, wherein $R^3$ is 2-(3,5-bis-trifluoromethylphenyl)-ethyl.

12. A compound according to claim 4, wherein $R^3$ is 2-(3,5-bis-trifluoromethylphenyl)-ethyl.

13. A compound according to claim 1, wherein the group —NR$^3$R$^4$ is

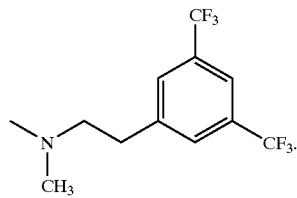

14. A compound according to claim 2, wherein the group —NR$^3$R$^4$ is

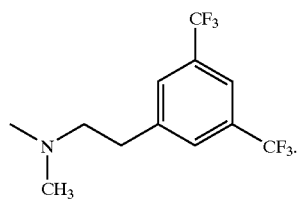

15. A compound according to claim 3, wherein the group —NR$^3$R$^4$ is

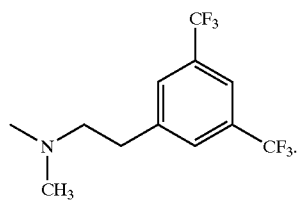

16. A compound according to claim 4, wherein the group —NR$^3$R$^4$ is

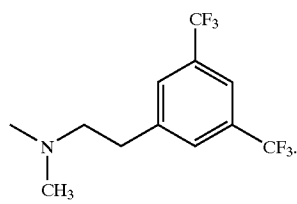

17. A compound according to claim 1, wherein
R$^1$ denotes a C$_1$–C$_3$-alkyl, phenyl or C$_1$–C$_3$-alkoxyphenyl group,
X denotes NH, and
R$^2$ denotes a hydrogen atom.

18. A compound according to claim 2, wherein
R$^1$ denotes a C$_1$–C$_3$-alkyl, phenyl or C$_1$–C$_3$-alkoxyphenyl group,
X denotes NH, and
R$^2$ denotes a hydrogen atom.

19. A compound according to claim 3, wherein
R$^1$ denotes a C$_1$–C$_3$-alkyl, phenyl or C$_1$–C$_3$-alkoxyphenyl group,
X denotes NH, and
R$^2$ denotes a hydrogen atom.

20. A compound according to claim 4, wherein
R$^1$ denotes a C$_1$–C$_3$-alkyl, phenyl or C$_1$–C$_3$-alkoxyphenyl group,
X denotes NH, and
R$^2$ denotes a hydrogen atom.

21. A compound of formula (I):

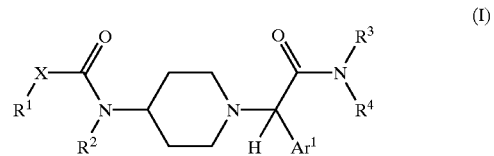

or a pharmaceutically acceptable salt thereof, wherein

R$^1$ and R$^2$ taken together denote an ethylene-1,2-diyl, 1-oxoethylene-1,2-diyl, propylene-1,3-diyl, 1-oxopropylene-1,3-diyl or 1-oxobutylene-1,3-diyl group, X denotes O, NH or NCH$_3$;

and Ar$^1$, R$^3$ and R$^4$ are as defined in claim 1.

22. A compound selected from the following compounds:

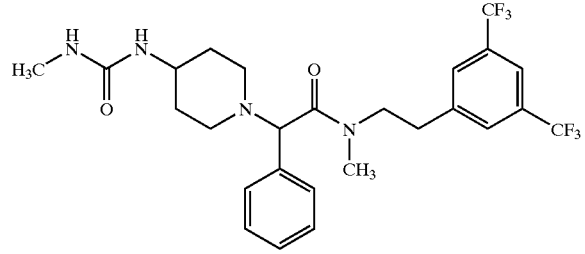

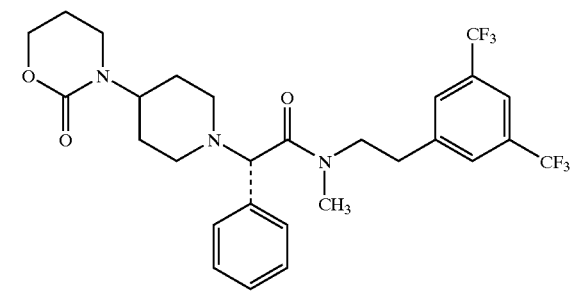

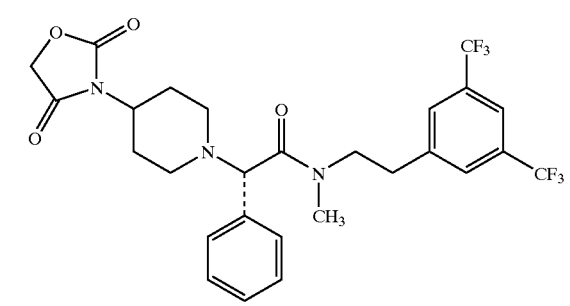

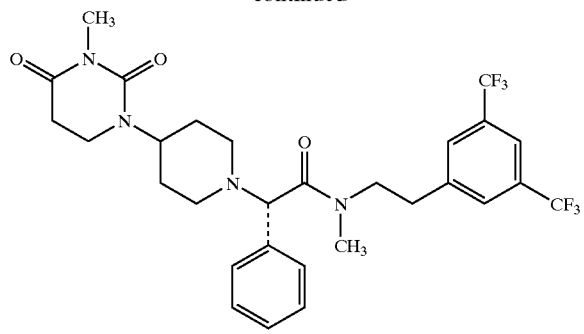

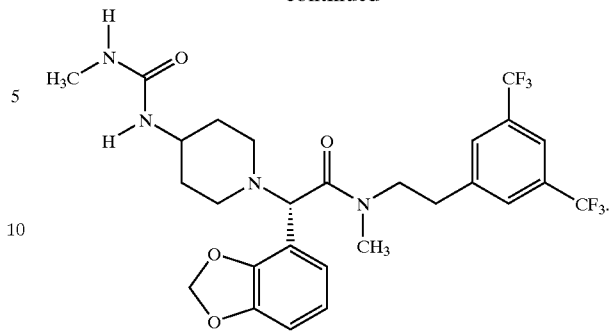

23. A process for preparing a compound of formula I according to claim 1 or 21, said process comprising reacting an amide of formula II

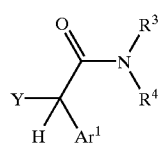

(II)

wherein Ar¹, R³ and R⁴ are as defined in claim 1 or 21, and Y denotes a suitable leaving group, with a piperidine of formula III:

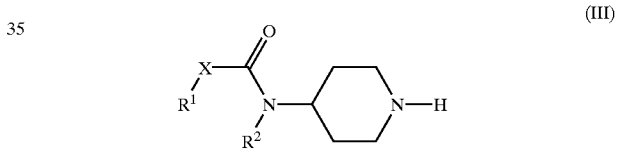

(III)

wherein $R^1$, $R^2$ and X are as defined in claim 1 and 21, in an inert solvent, optionally in the presence of a base.

24. A pharmaceutical composition comprising a compound according to one of claims 1 and 21 and one or more pharmaceutically acceptable carriers and excipients.

25. A method of treating an illness selected from inflammatory and allergic conditions of the airways comprising administering to a host in need of such treatment a therapeutically effective amount of a compound according to claim 1 or 21.

26. A method of treating an illness selected from asthma, chronic bronchitis, hyperreactive airways, emphysema, rhinitis, COPD, pulmonary hypertension, cystic fibrosis and coughs comprising administering to a host in need of such treatment a therapeutically effective amount of a compound according to claim 1 or 21.

* * * * *